United States Patent
Lewandowski

(10) Patent No.: US 6,309,676 B1
(45) Date of Patent: Oct. 30, 2001

(54) PET BREATH AMELIORATOR

(76) Inventor: Joan Lewandowski, HC 63, Box 60, Costigan, ME (US) 04223

( * ) Notice: Subject to any disclaimer, the term of this patent is extended or adjusted under 35 U.S.C. 154(b) by 0 days.

(21) Appl. No.: 09/356,601

(22) Filed: Jul. 19, 1999

Related U.S. Application Data

(63) Continuation-in-part of application No. 09/118,421, filed on Jul. 17, 1998, now Pat. No. 5,976,549.

(51) Int. Cl.$^7$ ............................. A61K 35/78; A61K 1/14; A23L 1/221
(52) U.S. Cl. ........................... 424/754; 424/442; 426/49; 426/54
(58) Field of Search ................................ 424/195.1, 442, 424/754; 426/49, 54

(56) References Cited

U.S. PATENT DOCUMENTS

| | | |
|---|---|---|
| 4,143,168 | 3/1979 | Bemotavicz . |
| 4,525,341 | 6/1985 | Deihl . |
| 4,763,604 | 8/1988 | Meekins . |
| 4,771,733 | 9/1988 | Axelrod . |
| 4,892,748 | 1/1990 | Andersen et al. ................... 426/635 |
| 5,405,836 | 4/1995 | Richar et al. . |
| 5,834,048 | 11/1998 | Erasmus et al. . |
| 5,976,549 | 11/1999 | Lewandowski ................... 424/195.1 |

FOREIGN PATENT DOCUMENTS

| | | | |
|---|---|---|---|
| 57193218 A | 11/1982 | (JP) | ............................... A61K/35/78 |

OTHER PUBLICATIONS

Matthew Hoffman, Ed.; Dogs. The Ultimate Care Guide, Rodale Press, Emmaus, 1998 citing Dr. Jan Bellows, DVM, PhD, p.408.

Mary L. Brennan, DVM; The Natural Dog. ISBN 0–45–227019–7, 1994, p. 97.

*Primary Examiner*—Marianne P. Allen
*Assistant Examiner*—Marjorie A. Moran
(74) *Attorney, Agent, or Firm*—Thomas L. Bohan; Patricia M. Mathers

(57) ABSTRACT

An oral hygienic compound and method for use in domesticated animals such as cats and dogs. The primary component of the oral hygienic compound is pure, natural garlic. The method involves coating or otherwise adulterating the animal's food with the oral hygienic compound in order to maximize garlic exposure within the oral cavity of the animal. Thus, the oral hygienic compound should promote chewing by the animal so as to evenly distribute the garlic within the animal's mouth. Garlic, in an uncooked state, has been found to substantially eliminate a pet's bad breath, whether by substantially reducing odor-causing bacteria within the oral cavity, and/or by other more systemic means when it is administered according to the inventive method.

14 Claims, No Drawings

PET BREATH AMELIORATOR

CROSS REFERENCE TO RELATED PATENT APPLICATION

This application is a continuation-part of Joan Lewadowski U.S. patent application Ser. No. 09/118,421, filed Jul. 17, 1998 now U.S. Pat. No. 5,976,549 for A METHOD TO REDUCE BAD BREATH IN A PET BY ADMINISTERING RAW GARLIC (title as amended). The content of this related patent application is incorporated herein by reference.

BACKGROUND OF THE INVENTION

1. Field of Invention

The present invention relates to the field of pet hygiene. More particularly, the present invention relates to controlling breath odor in pets. More particular yet, the present invention involves both a method and composition for controlling breath odor in pets such as dogs. Most particularly, the present invention involves the treatment and control of breath odor in pets by dispensing uncooked garlic in powder form to such pets.

2. Description of Prior Art

As all pet owners are aware, the smell of a pet's breath can be rank enough to repulse the pets' owners, as well as the owners' friends and relatives, thereby adversely affecting the emotional bond between dog and human. The cause of the bad breath is periodontal disease, caused by a build-up of plaque and tartar along the gumline and between the teeth of the pet. Plaque, a composition of bacteria, salivary proteins and food debris, builds up in the groove between the teeth and gums forming pockets in which bacteria can continue to breed and eventually damage the tissue surrounding the teeth. It is the bacteria that causes the malodorous breath of the pet. A veterinarian specializing in dental care in pets estimates that 98% of dogs with bad breath are suffering from periodontal disease. See Matthew Hoffman, Ed.; *Dogs. The Ultimate Care Guide*, Rodale Press, Emmaus, 1998, citing Dr. Jan Bellows, DVM, PhD, p. 408. The cause of bad breath in the remaining 2% of dogs that are not suffering from periodontal disease are systemic, or internal. For example, the bad breath may be the result of poor nutrition or organic dysfunctions that result noxious gases being discharged through the respiratory system. Just as there are remedies, such as breath mints, mouthwashes, pastes, and gels, intended for human use combating what the advertisers once dubbed "halitosis," so too are there similar "fresheners," i.e., cover-up liquids and solids, that can be administered to pets for what is referred to as "doggy breath." Some of these fresheners can be administered to the pet orally, others require that the pet owner apply the freshener to the oral cavity of the pet. Devices for applying the breath freshener include such things as dental wipes, scrubbers that fit over a person's finger, and toothbrushes and toothpaste specially formulated for pets. The difficulty with such devices is that the pet owner must apply the device to the pet's teeth, a task that may entail extensive time and energy. Using such means to clean a pet's teeth necessarily entails putting a foreign object into the oral cavity of the pet—an unnatural situation for the pet—and this may be distressful for the pet.

Oral sprays and cleansers are also known as breath fresheners, to be applied to the animal's oral cavity by the owner or by a veterinarian. In addition, there are various types of pet treats or toys that supply some type breath-freshening substance to the oral cavity of the pet. One such device is a treat that has a pumice-like substance on the surface of the treat which is used to remove tartar and plaque build-up from the pet's teeth as the pet chews the treat, e.g., BREATH TREATS FOR DOGS by FOUR PAWS. Other known devices are treats or chewy toys that contain breath-freshening ingredients such as mint, parsley, chlorophyl, vitamins, or zinc compounds.

In particular, Deihl (U.S. Pat. No. 4,525,341 issued Jun. 25, 1985) discloses a method of administering vitamins to air-breathing animals (including humans) by an aerosol vehicle that, in addition to containing vitamins, also contains a breath freshener. The aerosol of Deihl is sprayed into the nose or mouth opening of the animal from where some of it is carried to the lungs by the animal's respiration. The "breath freshener" of Deihl not being specified, it can be any one of the products on the market bearing that name. As with the dental wipes and toothbrush devices, the substance must be sprayed into the oral cavity and/or nasal cavity of the pet by the owner and may cause distress to the pet. The method of Deihl addresses the cause of the bad breath in only those few percent who have bad breath as a result of some systemic disorder; the administration of such aerosol "fresheners" does nothing more than temporarily mask the problem of bad breath in those pets suffering from periodontal disease.

Richar et al. (U.S. Pat. No. 5,405,836 issued Apr. 11, 1995) aver that a primary source of offensive breath in animals results from the breakdown of food proteins by bacteria in the oral cavity and disclose pet food containing water-soluble zinc compounds for controlling animal breath. Richar et al. teach that the zinc compounds can be incorporated into rawhide "chews" as a means of administering the bad-breath-controlling substance to the oral cavity. Zinc sulfate is one such zinc compound that is widely known as a deodorant. However, it is not entirely a benign substance. Although the amounts of the compound that must be ingested in order to cause illness or death in a human or other big animals are large, they are proportionately smaller in small pets, and much more care must be taken in dispensing a safe dose. Thus, although it is possible to administer such compounds safely by using informed care, the potential for harm is present, therefore compromising the benefit of this approach to bad-breath control.

Except for Richar et al., al of the other prior-art breath freshener for animals have relied on sweet mint or chlorophyll-based scents, sprays, dietary supplements, etc. to simply mask the bad odors that are present. As indicated, these methods have at best resulted in a temporary cover-up of the undesirable odors because they do not address the causes of periodontal disease, which is the cause of bad breath in 98% of dogs, for example; nor do they address systemic disorders that may be the cause of the bad breath in the remaining 2% of dogs with bad breath.

To the extent that offensive odors arise from the oral cavity alone, it is known that frequent scraping of plaque and tartar buildup from the animal's teeth is a further remedy, though one usually requiring the expertise and expense of a veterinarian, as animals frequently require sedation during such scraping. Many chewy devices rely upon a mechanical action for reduction of tartar and plaque, such as the above-mentioned FOUR PAWS BREATH TREATS with the pumice-like substance, or the numerous chewy devices for dogs that have nubbles or some other irregularity on the surface of the device to help scrape off tartar or plaque as the dog chews. While tartar and plaque removal is effective and beneficial from a dental perspective, the offensive odors from the pet's mouth are neither entirely eliminated, nor even reduced for an appreciable amount of time. One reason for this is that scraping does not eliminate the odor-causing bacteria, but only a particular breeding place for such bacteria.

Therefore, what is needed is a method that is effective in eliminating offensive breath in pets, particularly dogs, rather than merely masking offensive odor. What is yet further needed is such a method that can be easily administered by the pets' owners. What is still further needed is a breath-freshening device that is benign to both the pet and the environment. Finally, what is need is such a breath-freshening device that is acceptable to the pet.

SUMMARY OF THE INVENTION

The object of this invention is to provide a method that is effective in eliminating bad breath in domestic pets, particularly in dogs. It is a further object of the present invention to provide such a method that is uncomplicated and easy for the pet owner to administer. It is a yet further object of the present invention to provide a breath-freshening device that is benign to both pets and the environment. Finally, it is an object of the present invention to provide such a breath-freshening device that is acceptable to the pet.

The present invention arose from domestic canine feeding research conducted by the inventor that has led to the counterintuitive result that ingestion of raw garlic powder by dogs largely eliminates the bad breath that the subject animals otherwise regularly manifested.

Garlic-related products exist in many forms such as bulbs, whole cloves, and minced, chopped, crushed, liquefied, extracted, dried, and roasted preparations. In addition to its use as an ingredient in food for human consumption, garlic also has desirable attributes as a flavor-enhancer in pet foods. Garlic, in its many forms, is considered to have some therapeutic benefits, both for humans and for mammalian animals. The therapeutic benefits for pets derived from ingesting garlic are generally considered to be in promoting cardiovascular activity and providing a systemic insect repellent, and, in the field of pet hygiene, the primary use of garlic heretofore has been as a systemic flea repellant. Products relying on garlic for this purpose include "Garlic Pearls" offered by Hilton Canine Products and "Brewers Yeast With Garlic" offered by FOUR PAWS, which includes minute amounts of garlic. Due to the systemic nature of the use of such products, however, each product is designed to maximize ingestion of the garlic within the digestive tract of the animal. This is done by encapsulating or otherwise compressing the garlic within a pill or capsule. Accordingly, the ability of so-ingested garlic or garlic-related compounds to affect the oral and nasal cavities of the animal is limited at best. Even if enough raw garlic is introduced systemically to produce some benefit in controlling the systemic contribution to bad breath as a side-effect, these products by their nature will not aid in the control of bad breath caused by malodorous bacteria residing locally in the oral and nasal cavities.

When considering garlic with respect to mouth odors, the commonly understood problem is that of "garlic-breath" present in human beings who have eaten some quantity of cooked garlic. A variety of mouthwashes, digestive aids, and oral hygiene products exists, presumably to counter the malodorous effects of garlic on human breath. Prior-art solutions purport to operate by either ridding one's mouth and body of the garlic scent after consumption or by somehow extracting the odor-causing compounds from the garlic prior to ingestion, the underlying point being that garlic is the root-cause of the oral odor problem. Thus, any assumption that garlic would promote pleasant breath in any animal—e.g., cats and dogs—runs counter to the apparently overwhelming common knowledge and experience, including that within the field of pet breath amelioration.

The observation by the inventor that something had caused the breath of her several dogs of various sizes and age to become unoffensive provided the stimulus to experiment with food and eventually led to the inventor's discovery that raw garlic greatly improved bad breath in dogs (and, by extension, other mammals kept as pets). Since the dogs were regularly fed "people food" in the form of table scraps and cooking samples, which they craved, it seemed reasonable to the inventor to conclude that something in the food that the dogs had managed to beg from the cook was effecting a reduction in the dogs' bad breath. In order to identify which of the various daily cooking ingredients had caused the change in the dogs' breath, the inventor conducted a series of tests on her six dogs over testing periods of two days each. The medium upon which varied ingredients were placed was ground beef. The ingredients tested included:

1) onions browned in olive oil and mixed with fried ground beef.

2) garlic browned in olive oil and mixed with fried ground beef.

3) garlic and onions browned in olive oil and mixed with fried ground beef;

4) garlic and onions browned in olive oil and cooked with canned tomatoes (tomatoes being known for their ability to eliminate certain odors, such as skunk) and mixed with fried ground beef;

5) ground beef patties coated with onion powder and then broiled;

6) ground beef patties coated with garlic powder and then broiled;

7) ground beef patties coated with ground sage and then broiled.

Each of items #1 through #7, when cooled and fed to the dogs, produced no change in the dogs' bad breath. After considering these results, testing procedures were then re-evaluated, leading to the belief that certain spices introduced after cooking might have caused the elimination of the dogs'offensive breath. Accordingly, the following combinations were fed to the dogs over a testing period of two days for each recipe:

8) broiled ground beef patties sprinkled after cooking with onion powder;

9) broiled ground beef patties sprinkled after cooking with ground sage;

10) broiled ground beef patties sprinkled after cooking with Parmesan cheese;

11) broiled ground beef patty sprinkled after cooking with garlic powder.

None of items #8 through #10, when fed to the dogs, produced any change in the dogs'bad breath. However, feeding the dogs ground beef coated with garlic powder (Item #11) resulted in the elimination of all offensive dog breath odor. This phenomenon was observed to last well into the next day's feeding, as much as 24 hours later. Additional experiments have shown that the effect of garlic powder on a dog's breath lasts at least 48 hours and on occasion up to 72 hours. In order to verify the beneficial and counterintuitive results of using uncooked garlic to substantially eliminate bad breath in dogs, garlic powder was thereafter used to coat all the dogs' meals. This eliminated bad breath from all of the dogs tested. Further, upon ceasing the use of garlic powder on each dogs' meals, the bad breath returned after a few days.

To confirm these results, garlic powder was administered to two additional dogs and to two litters, each litter consisting of 6 puppies. In all 14 animals, bad breath—including "puppy breath"—was eliminated. Thus, garlic in its uncooked state was verified as means for eliminating bad breath in dogs.

It is not clear why the inventor's method works to eliminate bad breath. It is known that crushed garlic contains an enzyme, allinase, which is known to have some bactericidal effects. It is reasonable to suppose that some of the odors present in offensive breath are caused by bacteria present in the oral and nasal cavities and that the application of allinase through the medium of garlic kills that bacteria and hence the odor arising from them. Inventor's experiments have shown that delivery of raw garlic to the animal in a manner that will maximize the degree of direct contact of the garlic with the saliva, teeth, and tissue in the mouth cavity of the animal, eg., by sprinkling a coating of garlic powder on the animal's food, is effective in eliminating offensive mouth odor. It is important that the raw garlic coat the tissues and teeth of the pet, and mix with the saliva. Thus, biscuits, chewy snacks, or dry food that promote chewing and administer the garlic in a manner to increase the likelihood of direct contact of the garlic with the tissues, teeth, and saliva of the pet are suitable carriers for the raw garlic. In the case of dog food, "wet" or canned dog food is less suitable as a carrier, unless the garlic is applied topically to the food just prior to serving it, because of the ability of the dog to ingest wet food without chewing it, thereby reducing the amount of contact of the food with the tissues and teeth of the dog. Delivering raw garlic to an animal in a form that will allow the garlic to enter the animal's digestive tract without contacting to any large extent the teeth and tissue in the mouth cavity of the animal such as by delivering the garlic in a capsule, may provide some benefit in that the garlic may be effective systemically, i.e., killing odors that arise in the system of the animal, but it may not have the desired beneficial effect on offensive breath that is caused by the presence of odor-causing bacteria in the mouth. It is also significant that cooking (i.e., heating) the garlic destroys the desired effect on the animals' breath.

It is an object of the present invention to deliver raw garlic to a pet in a way that is both easy for the pet owner and acceptable to and safe for the animal. Thus, dispensing raw garlic powder from a special shaker onto the animal's food, for example, is one convenient method of achieving the desired effect. Alternatively, one can also prepare the surface of chewy devices such as rawhide products, dog biscuits, cat treats, and the like, for the delivery of the raw garlic cure to pets. Such devices can be coated with raw powdered garlic by applying the garlic with a high-powered spray gun to the baked products while they are still warm and moist from the oven, or rolling or shaking the devices in a container containing the raw garlic. The device may be coated first with a substance that will cause the garlic to adhere to it, or the raw garlic can be suspended in a gel or a paste. Similar ingenuity can be used to apply raw garlic, as dry powder or wet coating, for example, to such items as dog and cat toys, such as by coating catnip impregnated objects with the raw garlic.

Other ingredients may also be mixed in with and applied with the garlic powder to further enhance the therapeutic effects of the garlic. In some pets, ingesting raw garlic may cause flatulene, although this was not observed by the inventor in her experiments. The raw garlic powder coating may also include flatulence-reducing ingredients, such as fennel seed, caraway seed, ginger, celery seed, bloodroot, and other ingredients known to relieve flatulence in pets. It is known that pets like the flavor of garlic, thus, flavor-enhancing ingredients as a means of inducing the pet to use the device will generally not be necessary, although it is possible to add flavor-enhancers to the garlic coating.

Ingesting excessive quantities of garlic (or onion), raw or cooked, can cause Heinz-body anemia in pets and, therefore, the amount dispensed on the pet food must be appropriate for the body weight of the pet. Although it is not known that any veterinary colleges have conducted studies on the effects of garlic on pets, the suggested dosage of raw garlic that is generally considered to have therapeutic value for certain problems and also to be safe is approximately ½ clove of raw garlic per 10 lbs. of body weight. See *The Natural Dog* by Mary L. Brennan, D.V.M., ISBN 0-45-227019-7, 1994, p. 97. The therapeutic value cited in many sources of literature refers to the known beneficial effects of garlic as a deterrent to fleas. The inventor has determined that the amount of raw garlic necessary to be effective in eliminating bad odor in pets is not directly related to body weight of the pet, but rather, is the amount necessary to come into contact with the teeth, tissues, and saliva in the pet's mouth. The size of the mouth does not increase in direct proportion to the body weight of the dog. This is particularly true for very large dogs.

Suggested daily dosages of raw garlic powder sprinkled on dry dog food or applied to dog biscuits are shown in Table 1. Inventor has determined that these daily dosages are effective and are within the suggested levels that are safe regarding Heinz-body anemia.

BRIEF DESCRIPTION OF THE PREFERRED EMBODIMENT

The preferred method of administering the raw garlic to a pet is to apply a coating of garlic powder prepared from uncooked garlic to pet food and/or snacks. While allinase in its purified form, either extracted from garlic or synthetically produced, may indeed work to rid one's pet of bad breath in accordance with the present invention, the inexpensive and more natural form of powdered garlic is preferred. In the Preferred Embodiment of the present invention, the raw garlic is applied as a coating to biscuits during processing so that the coating is already in place when the pet owners purchase the pet food and snacks. This will ensure that the garlic is delivered consistently and in the appropriate amounts. A medium-to-large size dog, for example, weighing between 40 and 50 pounds, would then be fed eight medium-size garlic-coated dog biscuits over the course of the day, the coating of garlic on the eight biscuits containing a total of approximately ¼ teaspoon of raw garlic. The appropriate amounts to be applied to the dog biscuits in the Preferred Embodiment are given in Table 1. These are approximate amounts. It is important to keep in mind that the garlic must be sufficient to coat the teeth and oral cavity tissue and to mix with the saliva, to provide effective bactericidal coverage. Dry pet food or chewy snacks, coated with raw garlic, are also effective carriers for administering raw garlic to a pet.

TABLE 1

| Weight of Dog lbs. (kg) | Amount of Garlic teaspoon (milligram) | Number of Garlic-coated Biscuits (s = small; m = med.) |
| --- | --- | --- |
| 3–15 (1.5–7) | approx. ¹⁄₃₂ (up to 50) | 3–5 s or 2 m |
| 15–20 | ¹⁄₃₂–¹⁄₁₆ | 3–5 s or 2 m |

TABLE 1-continued

| Weight of Dog lbs. (kg) | Amount of Garlic teaspoon (milligram) | Number of Garlic-coated Biscuits (s = small; m = med.) |
|---|---|---|
| (7–9) | (50–100) | |
| 21–40 | 1/16–1/8 | 6–9 s or 3 m |
| (9–18) | (100–200) | |
| 41–50 | 1/8–1/4 | 10–12 s or 8 m |
| (18–23) | (300–400) | |
| 51–60 | 1/8–1/4 | 10–12 s or 8 m |
| (23–27) | (300–400) | |
| 61–80 | 1/4–3/8 | 10–12 s or 10 m |
| (27–36) | (400–600) | |
| 80–100+ | 3/8–1/2 | 12 m |
| (36–45+) | (600–800) | |

It should be understood that the Preferred Embodiment mentioned here is merely illustrative of the present invention. Numerous variations in the application of the present invention may be contemplated in view of the following claims without straying from the intended scope and field of the invention herein disclosed.

I claim:

1. A device for ameliorating bad breath in a pet, said device comprising a delivery medium having an external surface and raw garlic bonded to said external surface.

2. The device as claimed in claim 1 wherein the pet is a dog and an amount approximately equivalent to 1/4–1/2 clove of raw garlic per 10 pounds of body weight of said dog is bonded to a daily dog ration of said delivery medium.

3. The device as claimed in claim 2 wherein said garlic is in the form of garlic powder.

4. The device as claimed in claim 2 wherein said garlic is suspended in a liquid that is applied to said external surface.

5. The device as claimed in claim 2 wherein said delivery medium is in the form of a gel in which said garlic powder is suspended.

6. The device as claimed in claim 2 wherein said delivery medium is in the form of a paste in which said garlic powder is suspended.

7. A device for ameliorating bad breath in a pet, said device comprising a delivery medium having an external surface and raw garlic bonded to said external surface.

8. The device as claimed in claim 2 wherein said delivery medium is a chewable raw garlic delivery means made of a natural substance, said chewable delivery means having an outer surface, said outer surface being coated with said raw garlic.

9. The device as claimed in claim 2 wherein said delivery medium is a chewable object made of an artificial material, said chewable object having an outer surface, said outer surface being coated with said raw garlic.

10. The device as described in claim 1 wherein the pet is a cat and an amount approximately equivalent to 1/4–1/2 clove of raw garlic per 10 pounds of body weight of said cat is applied to a daily cat ration of said delivery medium.

11. The device as claimed in claim 10 wherein said garlic is suspended in a liquid that is applied to said external surface.

12. The device as claimed in claim 10 wherein said delivery medium is a dry cat food.

13. The device as claimed in claim 10 wherein said delivery medium is a container of catnip.

14. The device as claimed in claim 10 wherein said delivery medium is a chewable object.

* * * * *